United States Patent
Belhe et al.

(10) Patent No.: US 7,731,726 B2
(45) Date of Patent: Jun. 8, 2010

(54) SUTURE BASED VASCULAR CLOSURE APPARATUS AND METHOD INCORPORATING A PRE-TIED KNOT

(75) Inventors: Kedar R. Belhe, Minnetonka, MN (US); John Avi Roop, Crystal, MN (US); Catherine A. Pipenhagen, Chanhassen, MN (US)

(73) Assignee: St. Jude Medical Puerto Rico LLC, Caguas, PR (US)

( * ) Notice: Subject to any disclaimer, the term of this patent is extended or adjusted under 35 U.S.C. 154(b) by 994 days.

(21) Appl. No.: 10/726,994

(22) Filed: Dec. 3, 2003

(65) Prior Publication Data

US 2005/0121042 A1  Jun. 9, 2005

(51) Int. Cl.
*A61B 17/04* (2006.01)
(52) U.S. Cl. .................................. 606/144; 606/148
(58) Field of Classification Search ............ 606/138, 606/139, 144, 148, 113, 153; 289/2, 13, 289/7
See application file for complete search history.

(56) References Cited

U.S. PATENT DOCUMENTS

| | | | |
|---|---|---|---|
| 3,871,379 A | 3/1975 | Clarke | |
| 4,602,635 A | 7/1986 | Mulhollan et al. | |
| 4,641,652 A | 2/1987 | Hutterer et al. | |
| 4,760,848 A | 8/1988 | Hasson | |
| 4,923,461 A | 5/1990 | Caspari et al. | |
| 5,021,059 A | 6/1991 | Kensey et al. | |
| 5,129,912 A * | 7/1992 | Noda et al. ............... | 606/139 |
| 5,222,974 A | 6/1993 | Kensey et al. | |
| 5,282,827 A | 2/1994 | Kensey et al. | |
| 5,330,488 A * | 7/1994 | Goldrath .................. | 606/148 |
| 5,411,520 A | 5/1995 | Nash et al. | |
| 5,496,332 A * | 3/1996 | Sierra et al. ............... | 606/139 |
| 5,562,684 A * | 10/1996 | Kammerer ................ | 606/139 |
| 5,562,688 A * | 10/1996 | Riza ........................ | 606/148 |
| 5,643,292 A | 7/1997 | Hart | |
| 5,649,959 A | 7/1997 | Hannam et al. | |
| 5,662,681 A | 9/1997 | Nash et al. | |
| 5,722,981 A * | 3/1998 | Stevens .................... | 606/148 |
| 5,728,114 A | 3/1998 | Evans et al. | |
| 5,861,004 A | 1/1999 | Kensey et al. | |
| 5,935,147 A | 8/1999 | Kensey et al. | |
| 6,045,569 A | 4/2000 | Kensey et al. | |
| 6,059,800 A | 5/2000 | Hart et al. | |
| 6,090,130 A | 7/2000 | Nash et al. | |
| 6,132,439 A | 10/2000 | Kontos | |
| 6,136,010 A * | 10/2000 | Modesitt et al. ........... | 606/144 |
| 6,171,317 B1 | 1/2001 | Jackson et al. | |
| 6,179,863 B1 | 1/2001 | Kensey et al. | |

(Continued)

*Primary Examiner*—Julian W Woo
(74) *Attorney, Agent, or Firm*—Holland & Hart

(57) ABSTRACT

A pre-tied knot is used in conjunction with a vascular closure device to approximate tissue surrounding an opening in a corporeal vessel. The pre-tied knot is positioned on a proximal end of the suture such that a distal end of the suture can be inserted through the pre-tied knot to complete the knot. A typical medical procedure as contemplated by the present invention is performed through a sheath inserted through an opening in the vessel wall to access the inside of the vessel. The device used to perform the medical procedure is then removed from the sheath and a vascular closure device is inserted through the sheath to position a suture across the vessel opening. The pre-tied knot assists in approximating tissue surrounding the vessel opening.

28 Claims, 18 Drawing Sheets

U.S. PATENT DOCUMENTS 6,638,286 B1 * 10/2003 Burbank et al. ............. 606/144
6,746,457 B2 * 6/2004 Dana et al. .................. 606/148

2002/0147456 A1 * 10/2002 Diduch et al. ............... 606/144

* cited by examiner

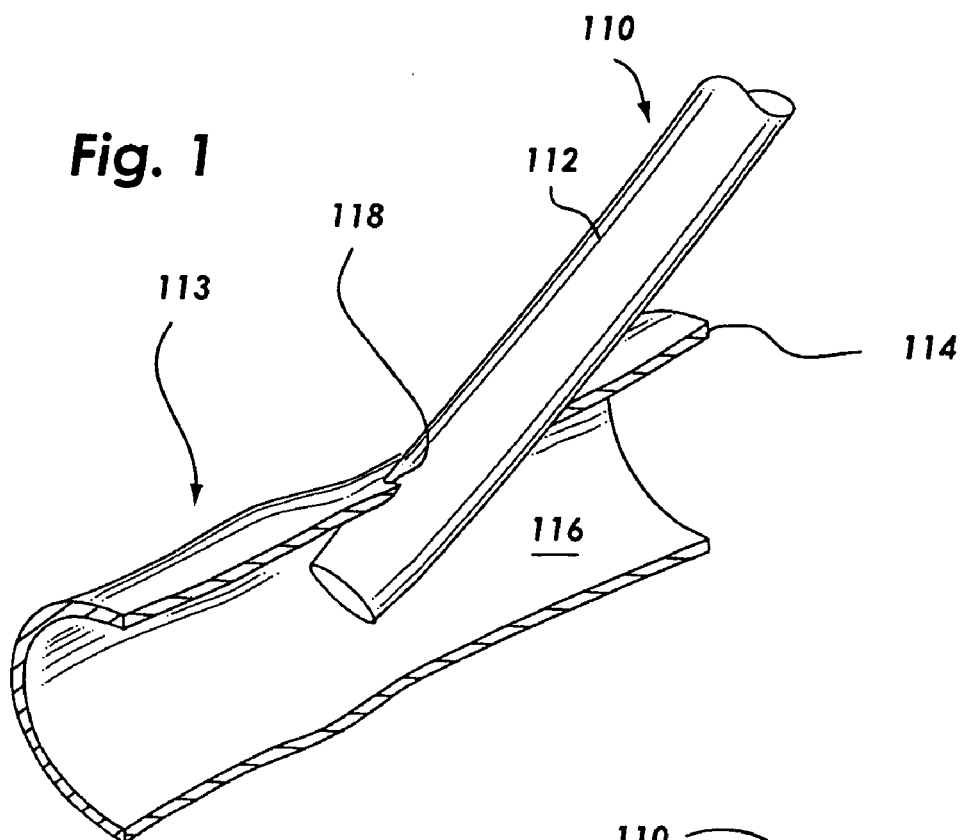
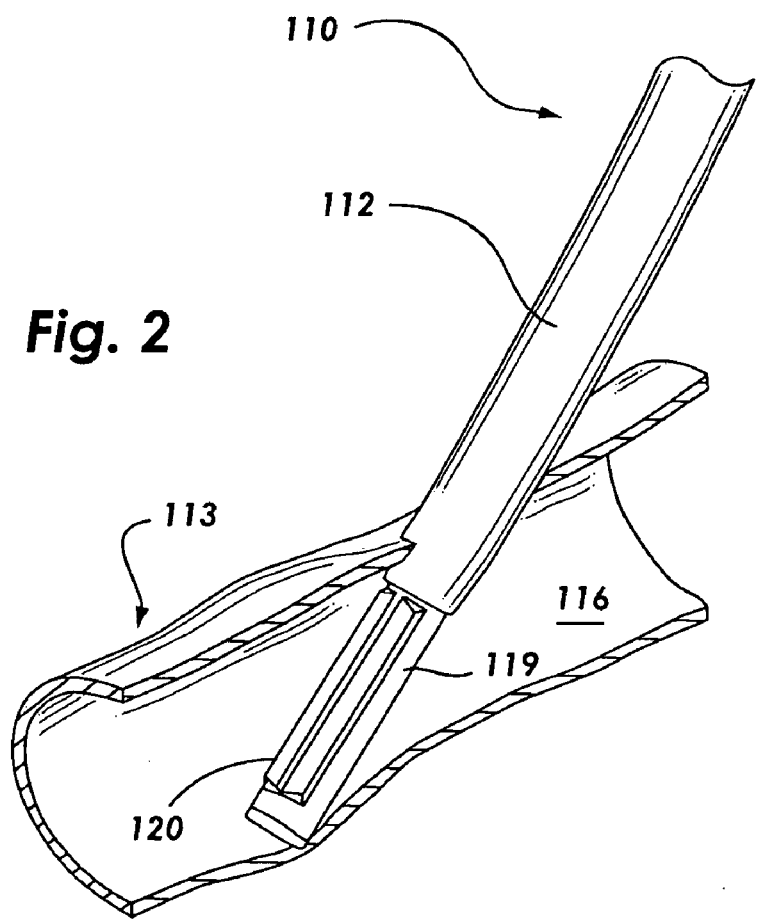

SUTURE BASED VASCULAR CLOSURE APPARATUS AND METHOD INCORPORATING A PRE-TIED KNOT

FIELD OF THE INVENTION

This invention relates to suturing devices. More specifically, this invention relates to suturing devices for approximating tissue surrounding an opening in a corporeal vessel wall.

BACKGROUND OF THE INVENTION

Various medical procedures, particularly cardiology procedures, involve accessing a corporeal vessel through a percutaneous sheath. The sheath necessarily requires the formation of a hole or opening in the vessel wall so that a medical procedure can be performed via the sheath. After the particular medical procedure has been performed, the sheath must eventually be removed from the vessel and the access hole in the vessel wall must be closed.

A number of prior vascular closure devices have been developed in attempting to provide a solution for the problem of closing a hole in the vessel wall. Tissue approximation typically involves passing a length suture into and through adjacent vessel and subcutaneous tissue, across the vessel opening, and back into and through adjacent vessel and subcutaneous tissue. Certain prior closure devices have involved relatively complicated methods and devices for extracting a length of suture from inside the vessel so that the physician can approximate tissue surrounding the hole in the vessel wall through use of the suture.

U.S. Pat. No. 5,643,292 and U.S. Pat. No. 6,059,800 disclose example prior suturing devices used for approximating tissue surrounding the opening in a vessel wall. Most prior closure devices enlarge the vessel opening thereby negating the benefits of using smaller or less invasive percutaneous products. Prior suturing devices are also relatively complicated and difficult to use.

There remains a need, therefore, to provide a suturing apparatus that is relatively simple in construction, is easy to use, and can effectively approximate tissue surrounding an opening in a vessel wall. There is further a need to provide a suturing device that minimizes the invasiveness of the suturing procedure.

SUMMARY OF THE INVENTION

The present invention involves utilizing a pre-tied knot in conjunction with a suturing device to approximate tissue surrounding an opening in a corporeal vessel. The novel pre-tied knot is positioned on the proximal end of the suture such that the distal free end of the suture can be inserted through the pre-tied knot thereby creating a complete knot. One device that may be used to approximate an opening in a vessel involves a snare or loop used to capture a free end of a suture within a vessel to approximate tissue surrounding an opening in a corporeal vessel. The apparatus involves two cannulae in the form of sharpened needles through which the suturing elements are deployed. A first needle is inserted through the vessel and through adjacent subcutaneous tissue on a first side of the vessel opening. A second needle is inserted through the vessel and through adjacent subcutaneous tissue on a second side of the opening. A snare or loop is carried by the first needle on the first side of the vessel. The snare is then deployed and precisely positioned to surround the opening of the second needle. After the snare has been properly positioned inside of the vessel, a suture, carried by the second needle, is extended into the vessel through an opening formed by the snare or loop. As the snare is retracted into the first needle, it closes around and grasps the suture. Eventually, the suture is pulled against the opening of the first needle. After the suture is properly placed across the vessel opening, the first and second needles are withdrawn from the vessel wall while the free end of the suture is held against the opening of the first needle and an additional length of suture is allowed to pass through the second needle and across the vessel opening as the needles are withdrawn. The free end of the suture is then guided through a coil of excess suture material to form a pre-tied knot. The pre-tied knot is then pushed down to cinch the suture and approximate tissue surrounding the opening.

The foregoing and other features, utilities, and advantages of the invention will be apparent from the following detailed description of the invention with reference to the accompanying drawings.

BRIEF DESCRIPTION OF THE DRAWINGS

FIG. 1 is a perspective view, partly in section, of a sheath extending through an opening in a vessel wall through which a medical device may be inserted for performing a medical procedure;

FIG. 2 is a perspective view, partly in section, of the sheath of FIG. 1 with a vascular closure device being extended out from the sheath;

DETAILED DESCRIPTION OF THE INVENTION

Figure 3:
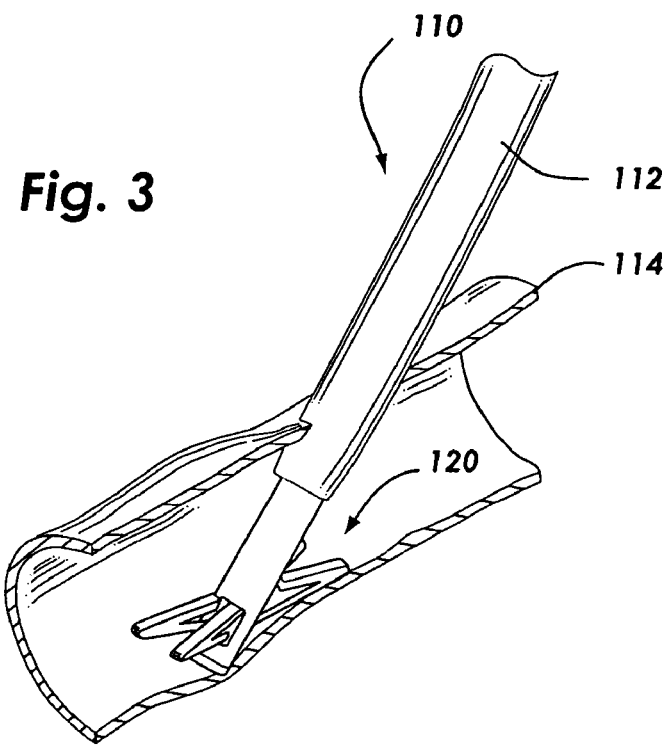
FIG. 3 is a perspective view, partly in section, of the vascular closure device of FIG. 2 with laterally extending feet being deployed from the vascular closure device to allow tactile feedback in determining the location of the sheath relative to the vessel wall.

The present invention involves a novel pre-tied knot to be used in conjunction with a device to approximate tissue surrounding an opening in a corporeal vessel. The novel pre-tied knot is formed at the proximal end of the suture device such that a distal end of a suture, after positioned across the vessel opening for tissue approximation, can be drawn back toward the proximal end of the suture device and inserted through the pre-tied knot to complete the knot. The present invention contemplates that a medical procedure will be performed through a sheath inserted through an opening in the vessel wall to access the inside of the vessel. After the medical procedure, the device used to perform the procedure is removed from the sheath and a vascular closure device is inserted down through the sheath to access the inside of the vessel. The closure device deploys a suture across the vessel opening. The closure device includes a pre-tied knot that is used to tie the suture and approximate tissue surrounding the vessel opening.

FIG. 1 shows a sheath 112 extending through an opening 118 in a vessel wall 114 to access the interior or inside 116 of the vessel 113. Opening 118 in the vessel wall 114 is required to accommodate sheath 112. Various types of medical procedures may be performed via sheath 112, after which the opening 118 and surrounding tissue (not shown) must be approximated to close the opening 118 in the vessel 113. The suture or closure device according to the present invention uses the same sheath 112 used to perform a medical procedure to also deploy a vascular closure device 119 to approximate tissue surrounding a vessel opening. By using the same sheath 112 for both procedures, the size of opening 118 may be minimized.

Figure 4:
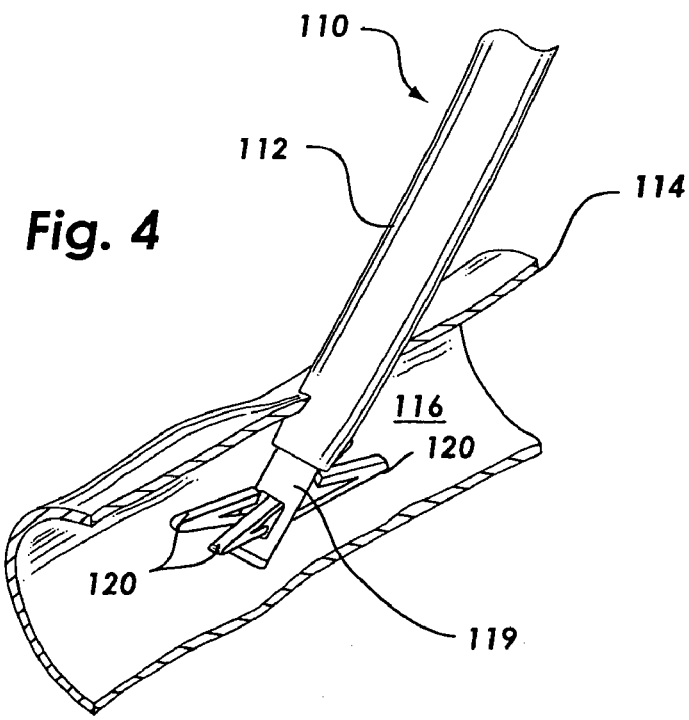
FIG. 4 is a perspective view, partly in section, of the vascular closure device of FIG. 2 being retracted or anchored against the vessel wall.

FIG. 2 illustrates the vascular closure device 119 extending beyond the distal end of the sheath 112 and into the interior 116 of the vessel 113. The vascular closure device 119 and sheath 112 are included as part of the vascular closure system 110. As shown in FIGS. 2-4, a plurality of feet 120 are deployed from the vascular closure device 119 to extend laterally so that the vascular closure device 119 can be retracted and the feet 120 will engage the inside surface of the vessel wall 114 and provide tactile feedback to the user of the device. Such tactile feedback informs the user of the depth of the closure device 119 relative to the vessel wall 114.

Figures 5, 6:
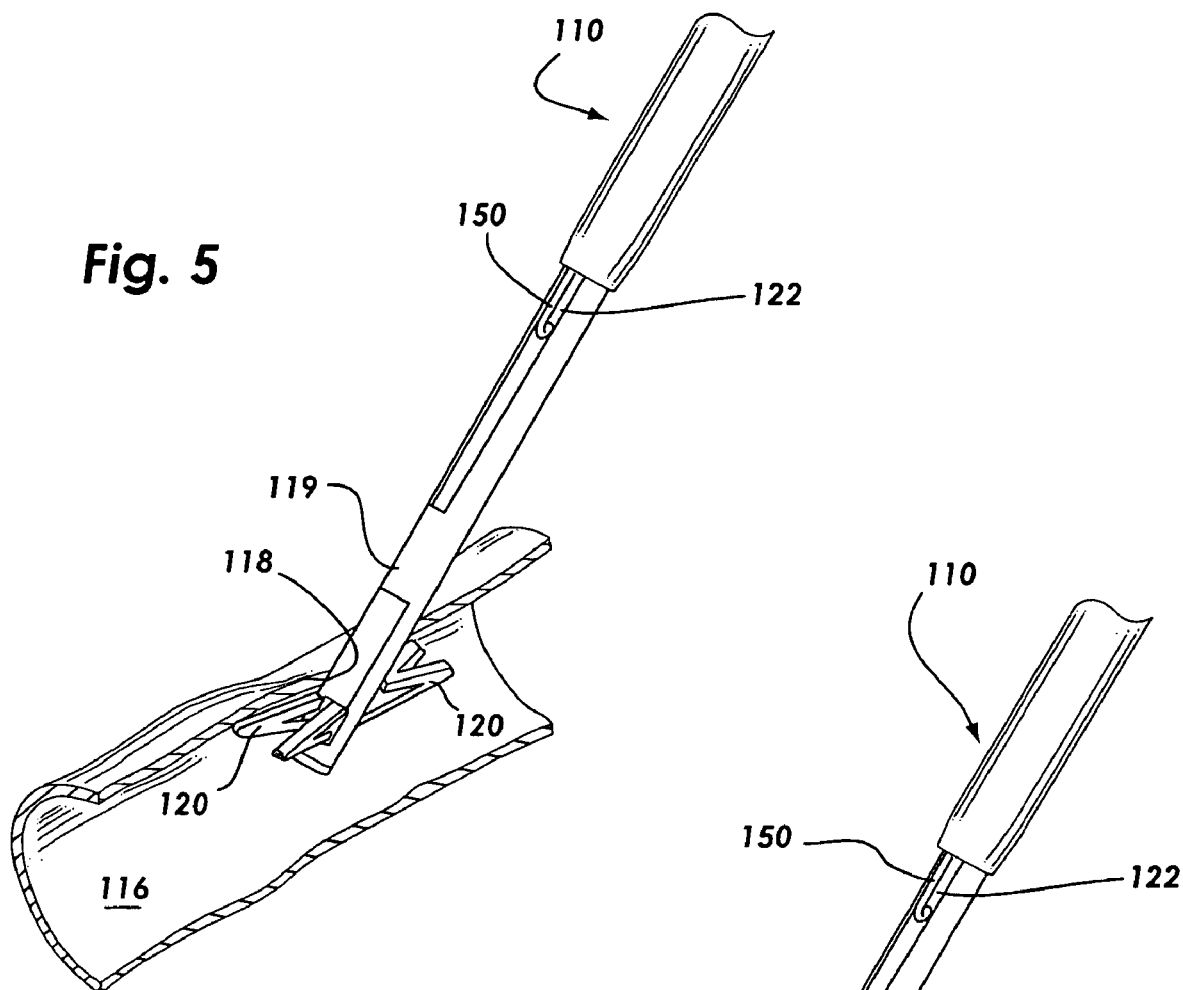
FIG. 5 is a perspective view, partly in section, of the vascular closure device of FIG. 2 wherein the sheath is retracted proximally to reveal first and second integrated needles (only the second needle is shown)
FIG. 6 is a perspective view, partly in section, of the vascular closure device of FIG. 2 wherein the first needle is deployed on a first side of the vessel opening.

As shown in FIGS. 5 and 6, after the closure device 119 is inserted into the vessel openings, the sheath 112 is then retracted proximally relative to the position of the closure device 119 to expose a pair of sharpened cannulas or needles 122, 124 on opposite sides of the vascular closure device 119. The pair of sharpened needles 122, 124 are inserted through the subcutaneous tissue (not shown) adjacent the vessel wall 114 so that their respective distal ends 126, 128 extend into the inside 116 of the vessel on opposite sides of the opening 118. The needles provide passageways 130, 132, respectively, for carrying or allowing insertion of certain suture implements (discussed below). The needles 122, 124, in one embodiment, form an integral part of the vascular closure device 119 such that when the feet 120 are deployed and the depth of the vascular closure device 119 relative to the vessel wall 114 is determined, precision depth insertion of needles 122, 124 through the vessel wall can be accomplished to ensure that the distal ends 126, 128 are properly positioned beyond the vessel wall 114 on opposite sides of the vessel opening 118. Preferably, the needles 122, 124 will extend at an angle away from the suture device body 119. An angle of 3° to 20° may be utilized, with an angle range of 5° to 6° being preferred.

Figure 7:
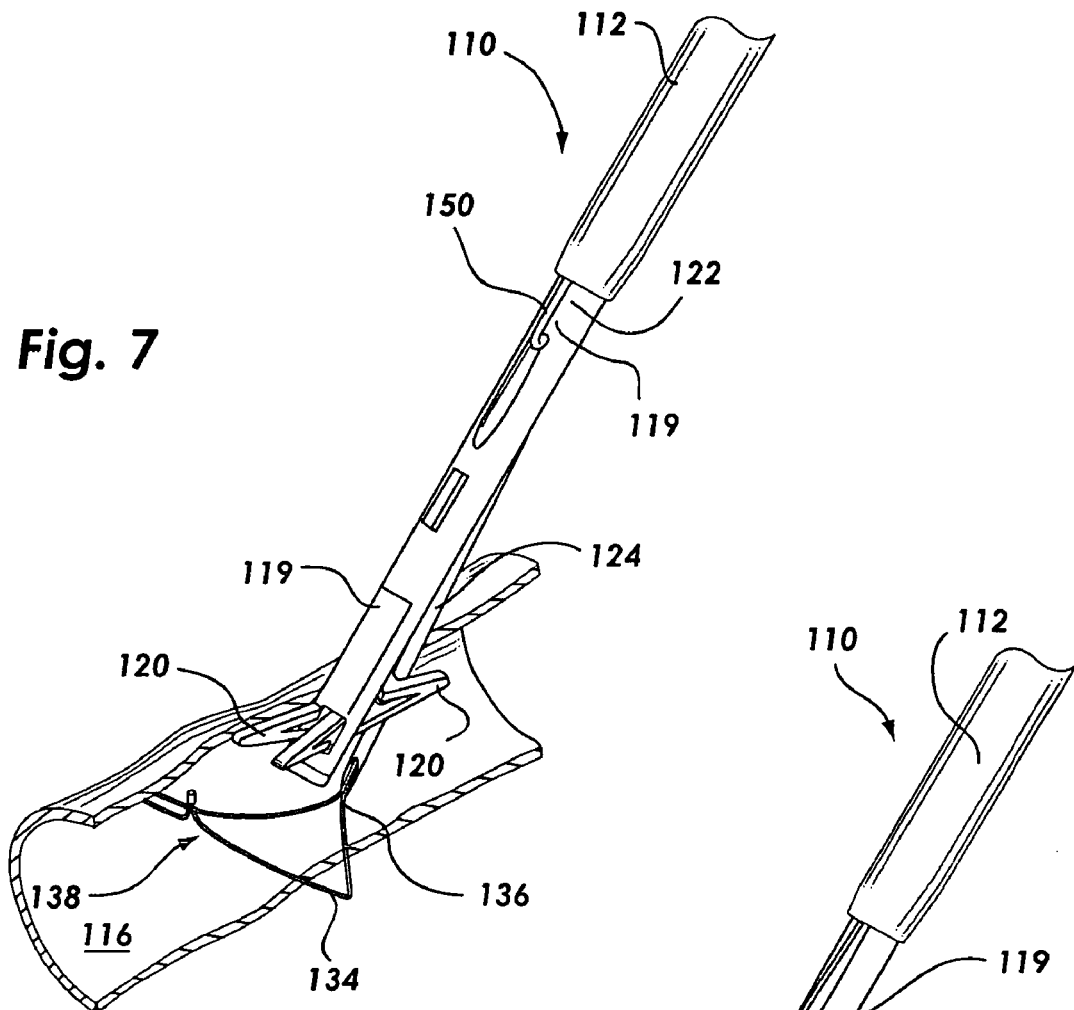
FIG. 7 is a perspective view, partly in section, of the vascular closure device of FIG. 2 wherein a snare is deployed from the first needle.
Figure 8:
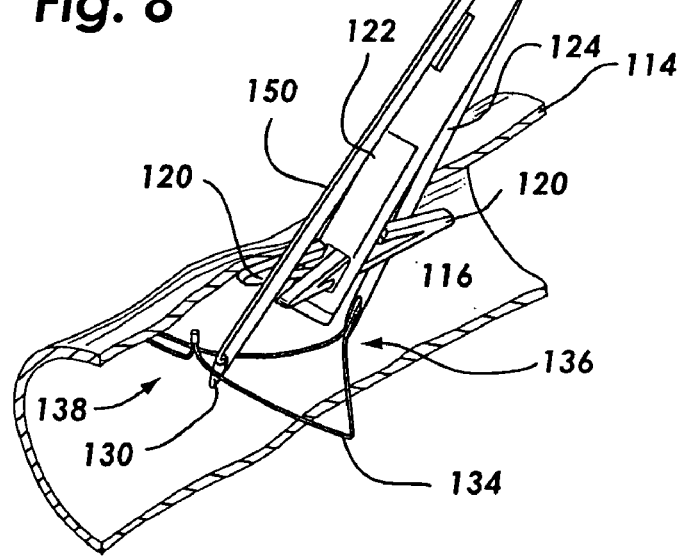
FIG. 8 is a perspective view, partly in section, of the vascular closure device of FIG. 2 wherein the second needle carrying a suture is being extended through a second side of the vessel opening and into the loop created by the snare.

After the needles 122, 124 have been deployed and extend through the vessel wall 114, a snare 134 in the form of a wire loop, carried by needle 124, is extended beyond the distal end 128 of needle 124, as shown in FIG. 7. The snare 134 is extended by a specific amount that is controlled by a hard stop mechanism. As shown in FIGS. 7 and 8, the snare 134, after it has been completely inserted past the opening 132 of needle 124, assumes a three-dimensional loop configuration having a proximal end 136 and a distal end 138. The proximal end 136 may be formed by two separate wires held together by some type of fastening device, such as a tube. The fastening device that secures the two wires together to form the loop should be sized so that it can move through the passageway provided by needle 124. The distal end 138 of wire loop 134 may be held together by a band or other fastener that is welded, crimped, or otherwise secured to the ends of the wires that comprise the loop 134. The fastening device for the distal end 138 should also be sized so that it can freely move inside the passageway formed by needle 124.

The snare or loop 134 may be made of a nickel/titanium alloy and will preferably have shape memory characteristics such that the configuration upon deployment is predictable and repeatable. Those skilled in the art will understand that other materials may be used to form the loop 134 without departing from the scope of the present invention.

When the snare or wire loop 134 is pulled inside of the first needle 124, the wires that comprise loop 134 are pulled together and are held in a side-by-side manner within the needle 124. When the wires that comprise loop 134 are pushed completely outside of the opening 132 of needle 124, the distal end 138 first moves along the bottom of the inside 116 of the vessel, after which the wire flips up to surround the opening 126 of needle 122. This "flipping" or pivotal movement of the loop 134 prevents interference with the suture device body 119 and the needle 122. When the loop 134 is deployed and the opposed wires that comprise the loop 134 are spread away from each other, the opposed wires take on a three-dimensional shape (as compared to the two-dimensional side-by-side shape the wires assume when inside of needle 124). When the loop is deployed inside the vessel, the distal end 138 of the wire loop 134 assumes, in one embodiment, a generally V-shaped configuration.

Figure 9:
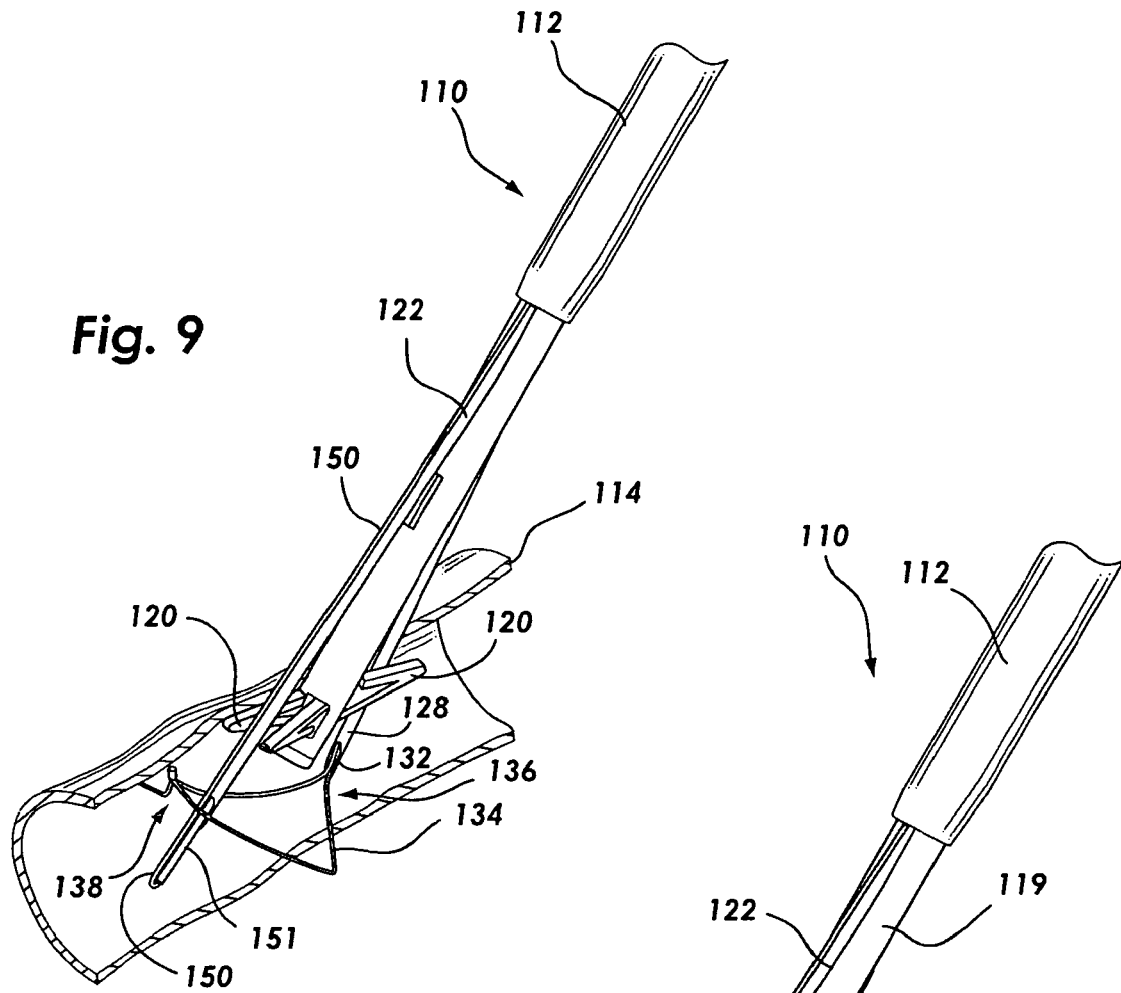
FIG. 9 is a perspective view, partly in section, of the vascular closure device of FIG. 2 showing a free end of the suture being extended beyond the opening of the second needle and into the loop formed by the snare.
Figure 10:
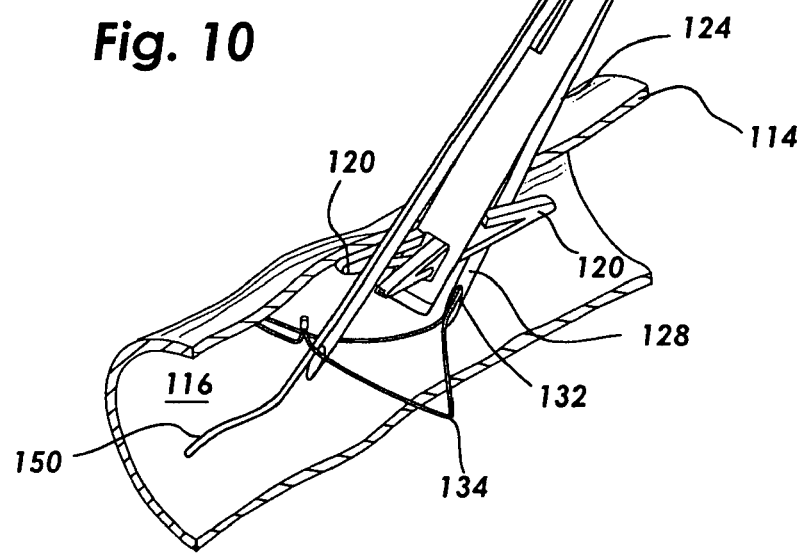
FIG. 10 is a perspective view, partly in section, of the vascular closure device of FIG. 2 showing the free end of the suture being released from the second needle and extending through the loop formed by the snare.
Figure 11:
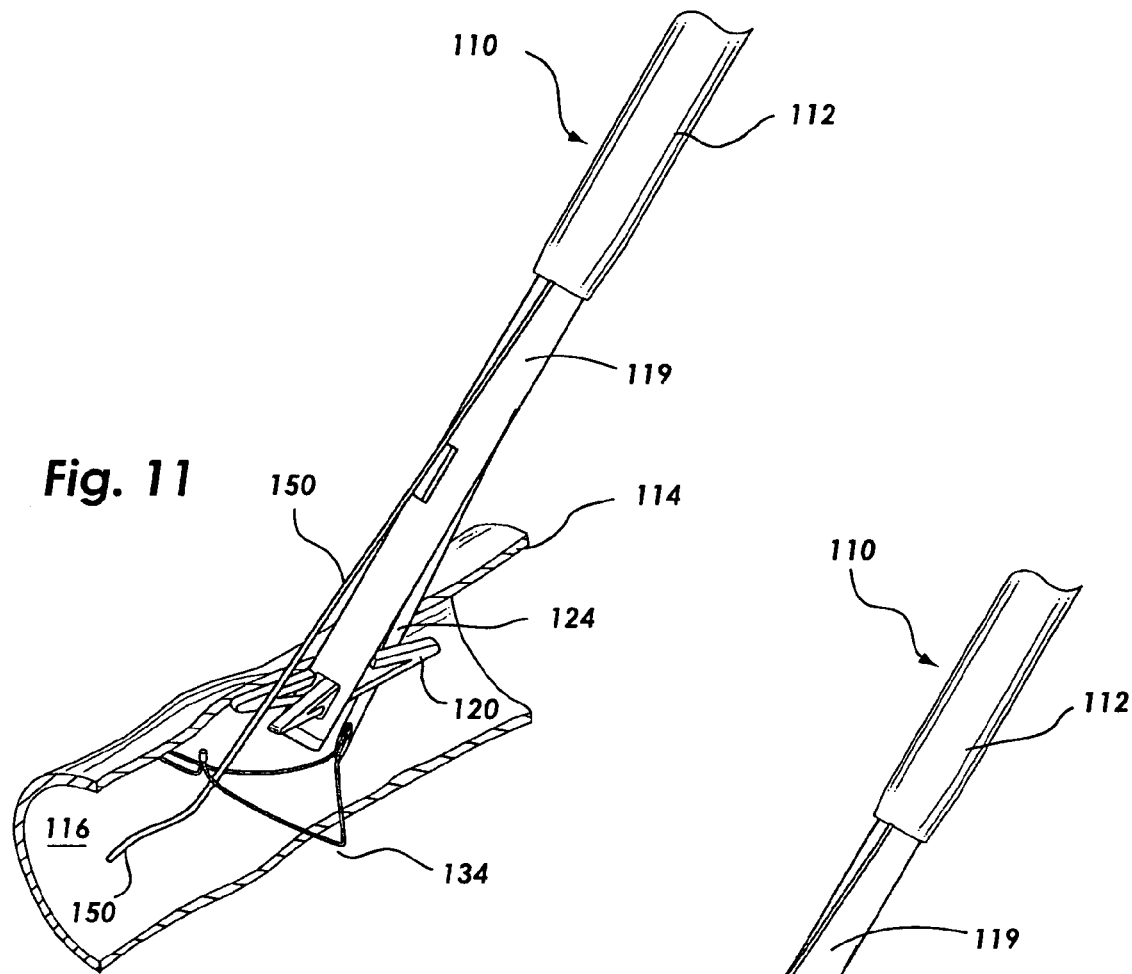
FIG. 11 is a perspective view, partly in section, of the vascular closure device of FIG. 2 wherein the second needle has been retracted back into the vascular closure device and the suture remains exposed along its length with a free end extending through the loop formed by the snare.
Figure 12:
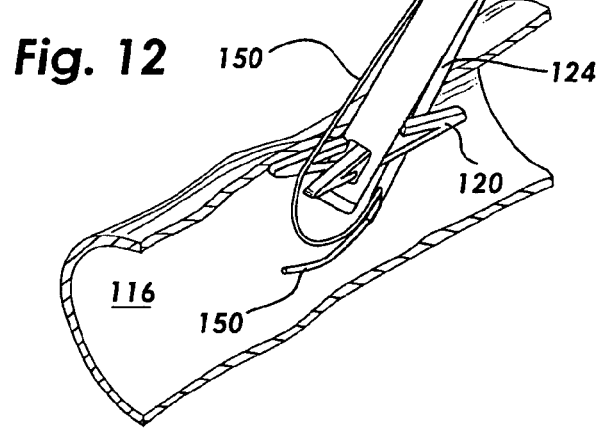
FIG. 12 is a perspective view, partly in section, of the vascular closure device of FIG. 2 showing the snare grasping the free end of the suture and pulling the suture against the opening of the first needle.

When a suture 150 (FIGS. 8 through 12) is inserted via second needle 122, the suture 150 extends through the area defined by the snare or wire loop 134. The suture 150 extends proximally down the second needle 122 and through the snare 134 with a suture pusher 151, as shown in FIG. 10. The suture 150 is extended by a specific amount that is controlled by a hard stop mechanism. The suture pusher 151 (FIG. 9) is a hollow semi rigid cylindrical member that fits within the second needle 122. The enclosed area within the snare 134 is configured such that when the snare 134 is retracted or pulled into opening 128 of needle 124, the wire loop 134 closes and the enclosed area of the snare 134 restricts around suture 150 to grasp or capture the suture and allow the suture 150 to be pulled firmly against the opening of the first needle 124, as shown in FIG. 12.

Figure 13:
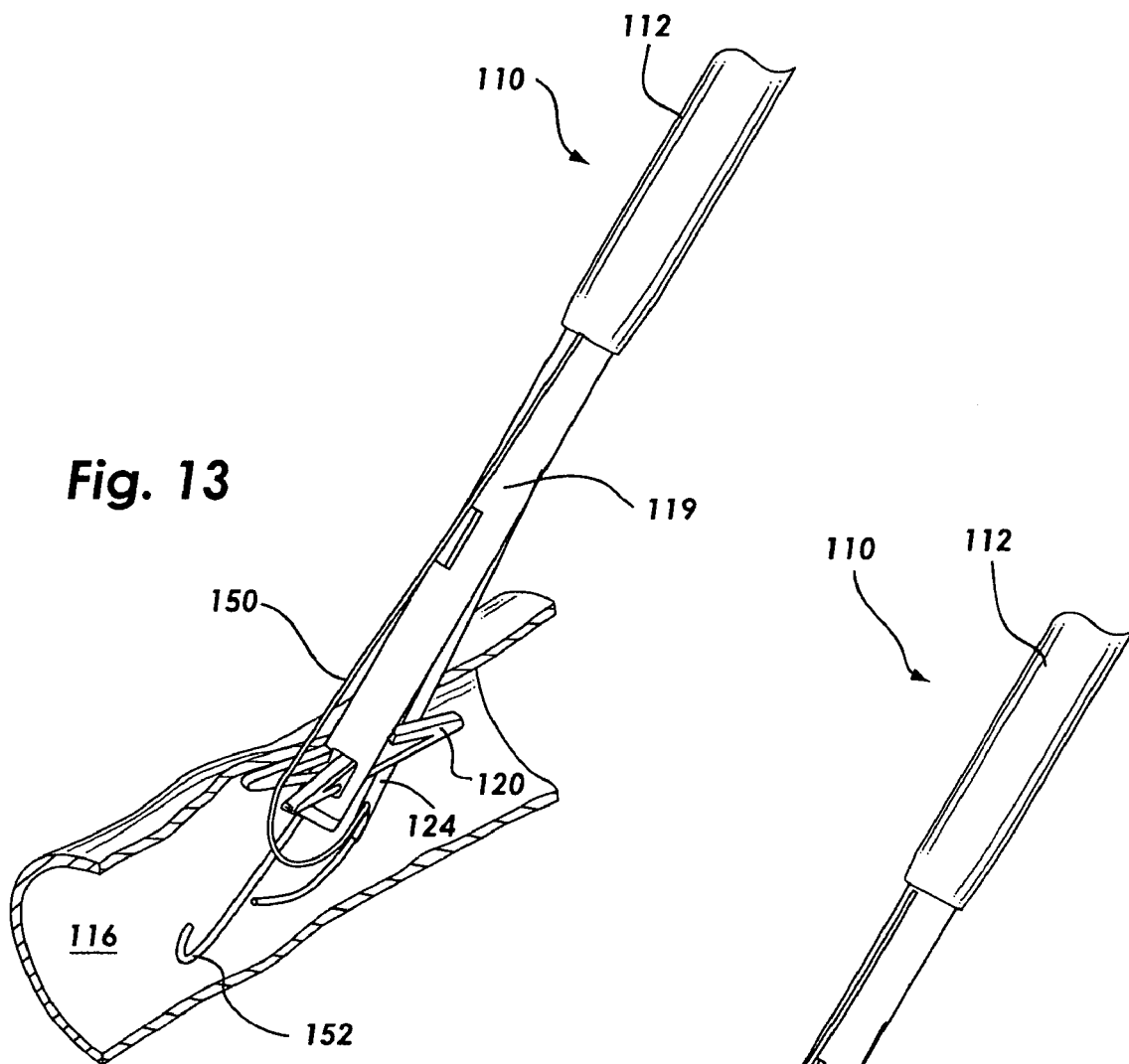
FIG. 13 is a perspective view, partly in section, of the vascular closure device of FIG. 2 showing a safety wire being deployed from the vascular closure device into the vessel.

FIG. 13 shows a safety wire 152 extending through the sheath and through the opening 118 in the vessel wall 114. The wire 152 provides a safety mechanism in case the suture is accidentally released. The safety wire 152 also provides a mechanism by which a second sheath could be properly inserted into the vessel opening 118 if the current vascular closure system 110 fails to properly seal the opening 118. In the illustrated embodiment, the safety wire 152 includes a J-tip on its distal end to prevent damage to the vessel wall 114.

Figure 14:
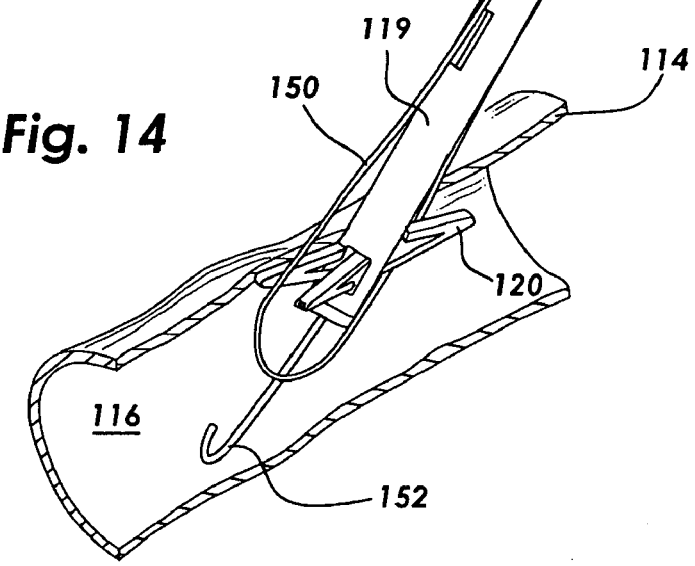
FIG. 14 is a perspective view, partly in section, of the vascular closure device of FIG. 2 showing the first needle being retracted into the vascular closure device.
Figure 15:
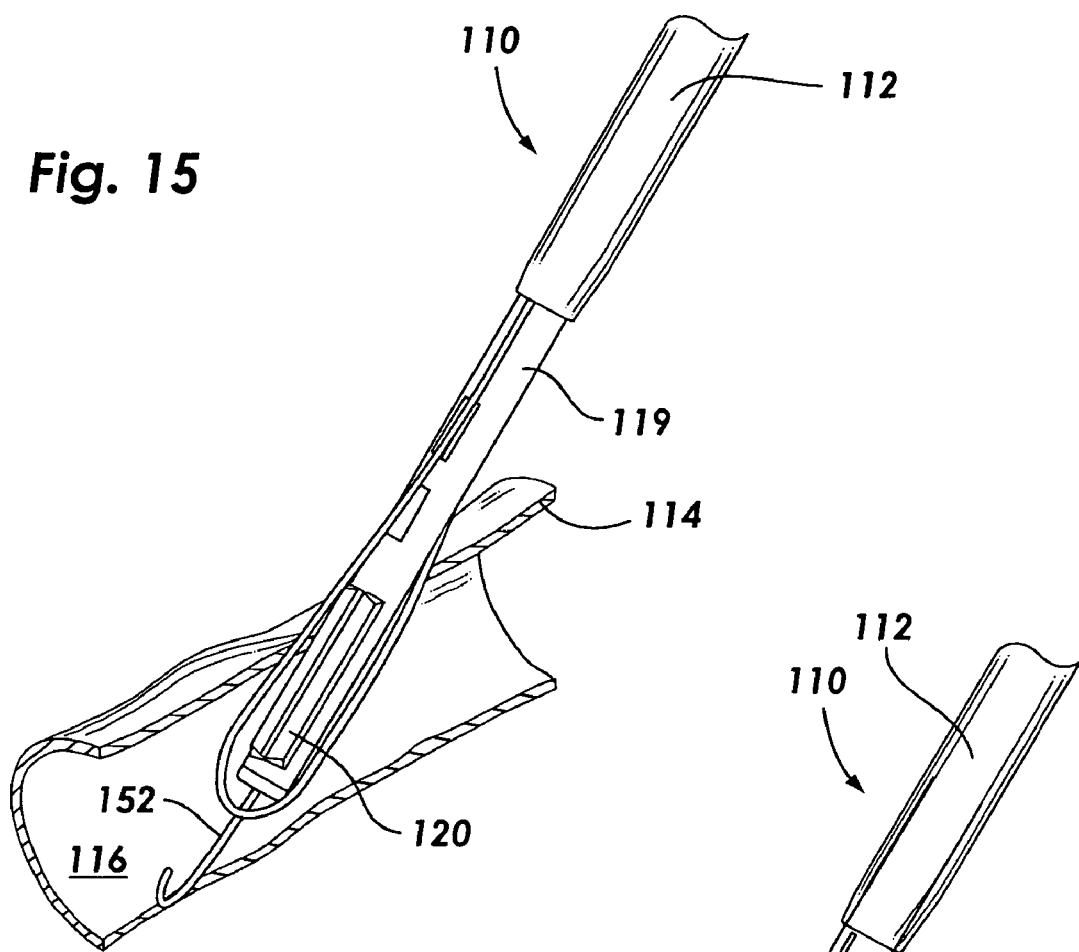
FIG. 15 is a perspective view, partly in section, of the vascular closure device of FIG. 2 showing the feet being retracted into the vascular closure device.
Figure 16:
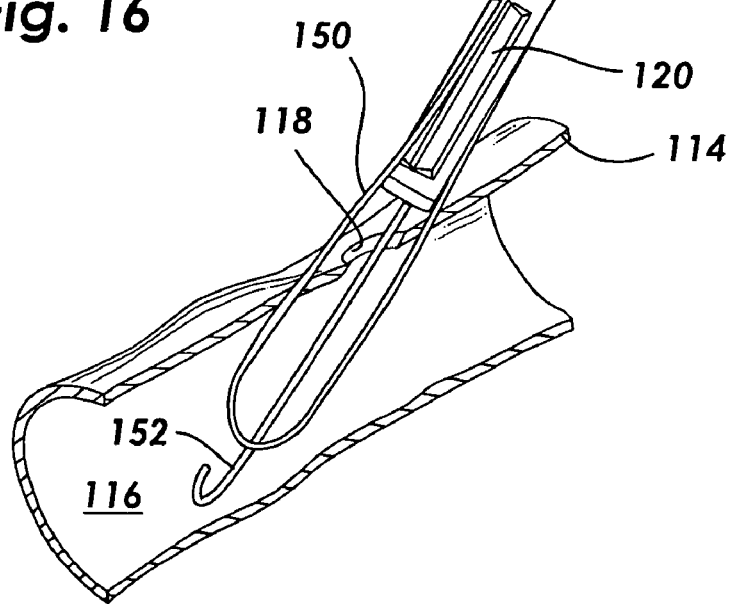
FIG. 16 is a perspective view, partly in section, of the vascular closure device of FIG. 2 showing the vascular closure device being retracted from the vessel opening leaving the safety wire extending through the vessel opening and the suture extending across the vessel opening.
Figure 17:
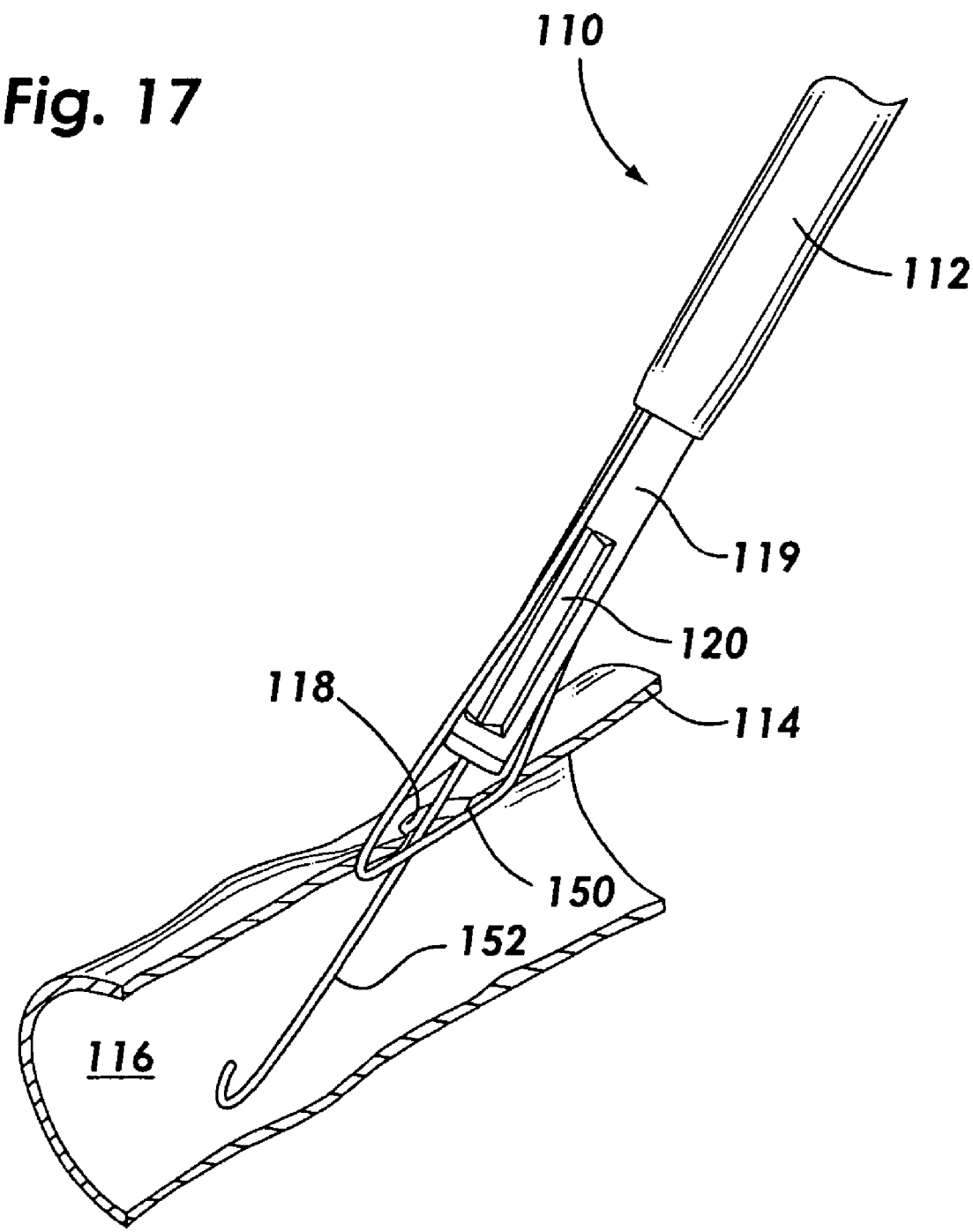
FIG. 17 is a perspective view, partly in section, of the vascular closure device of FIG. 2 showing the suture being tightened across the vessel opening.

After deployment of safety wire 152, the first and second needles 122, 124 are then retracted proximally back into the vascular closure device 119 as illustrated in FIG. 14. The suture 150 remains on the outside of the vascular closure device 119 but extends from and returns to the inside of the sheath 112. The feet 120 are subsequently retracted into the vascular closure device 119, as shown in FIG. 15. The entire suture based vascular closure system 110 (i.e., the sheath 112 and the closure device 119) can then be withdrawn from the opening 118 in the vessel 113, as shown in FIG. 16. FIG. 17 illustrates suture 150 extending across the vessel opening 118.

Figure 18:
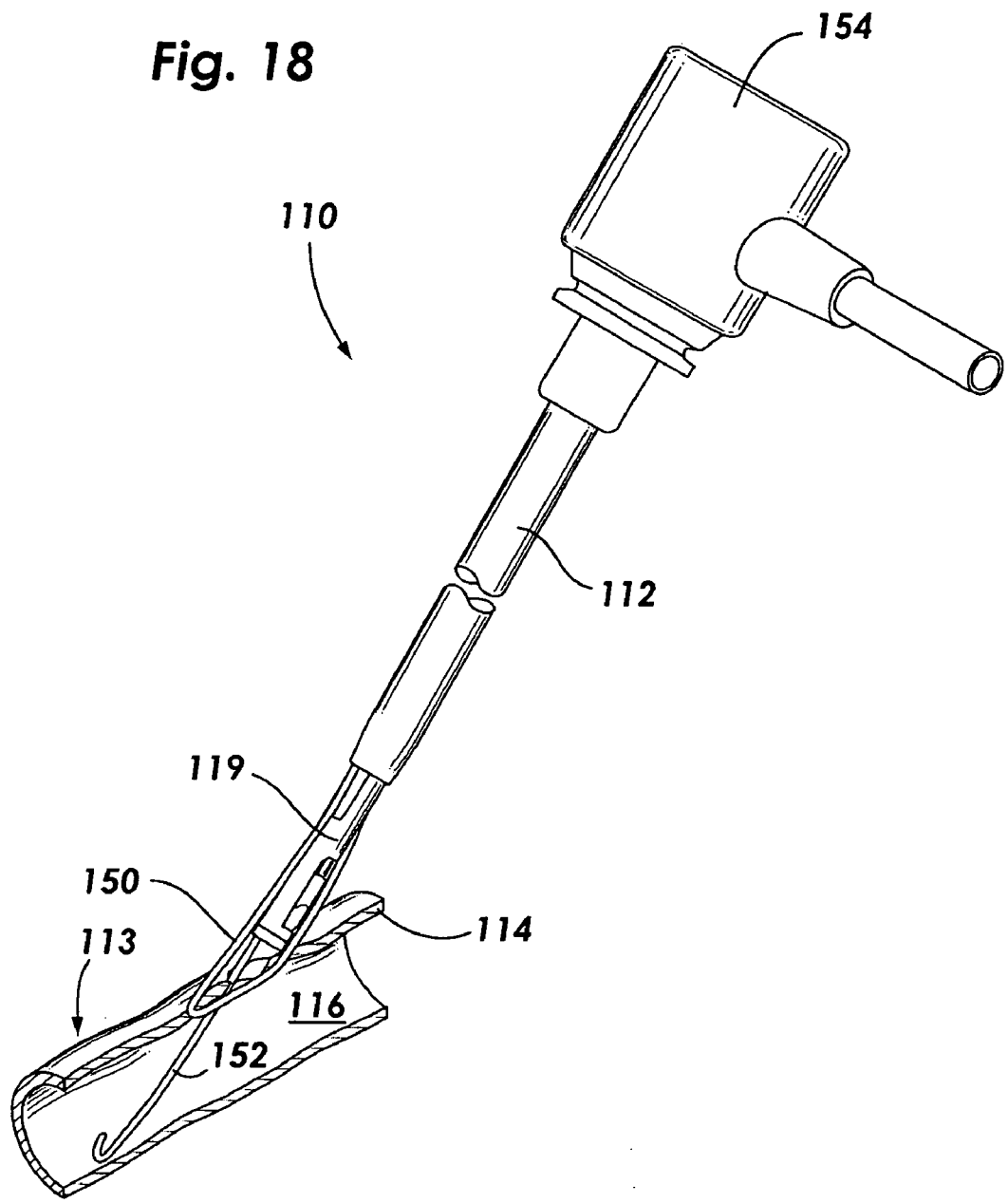
FIG. 18 is a perspective view, partly in section, of the vascular closure device of FIG. 2 and further illustrating a hub portion coupled to the sheath.

FIGS. 18 through 25 illustrate additional mechanisms utilized in combination with the vascular closure system 110 to deploy the pre-tied knot according to the present invention. Alternative embodiments may include other mechanisms for use in performing the described process and remain consistent with the teachings of the present invention. FIG. 18 shows a hub assembly 154 attached to the sheath 112. The hub assembly 154 includes a silicone valve that allows certain medical devices to be deployed via the sheath 112 while preventing blood and other body fluids from leaking out the sheath 112.

Figure 19:
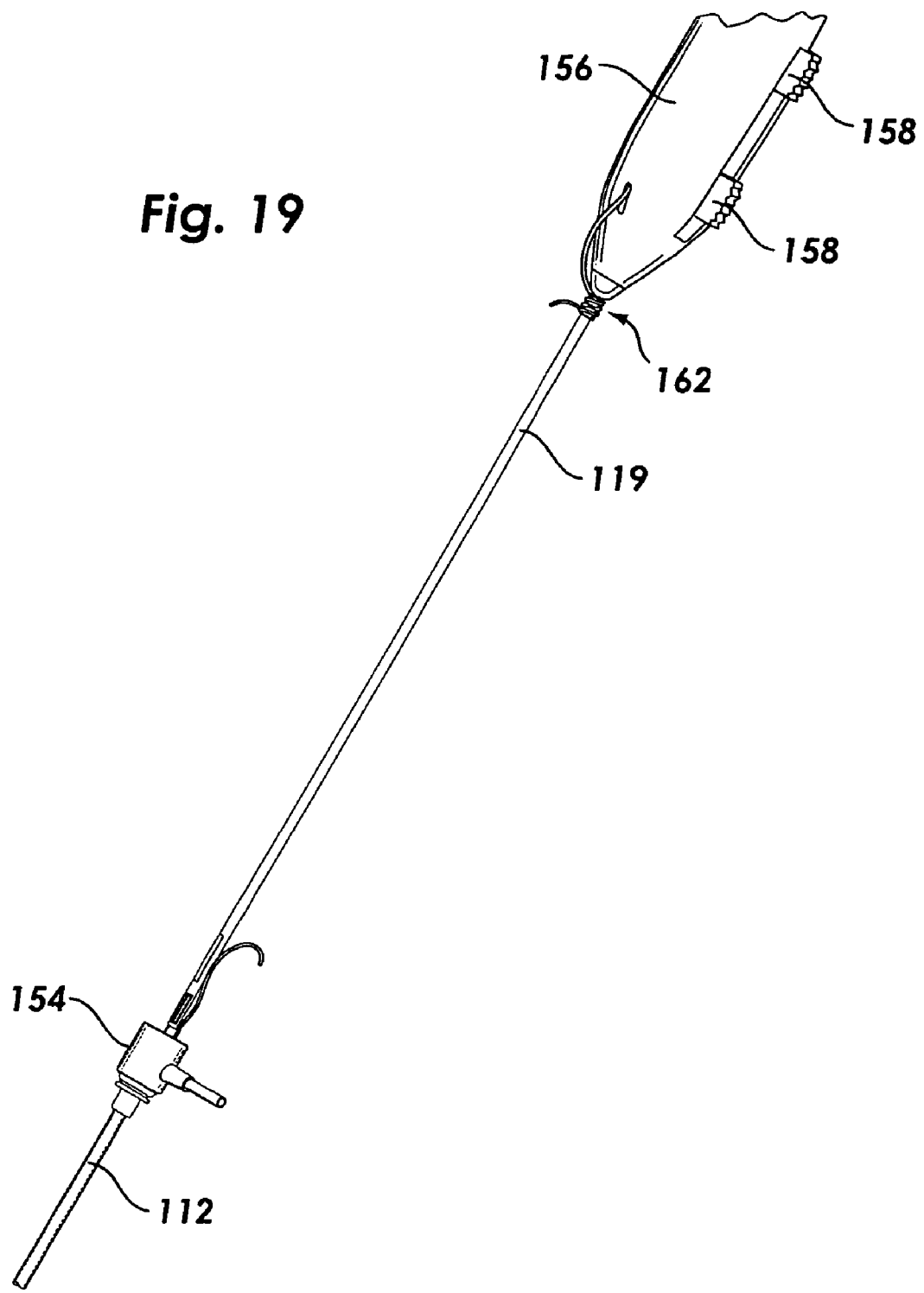
FIG. 19 is a perspective view, partly in section, of the vascular closure device of FIG. 2 and further illustrating a hub portion and a handle set operatively coupled to the sheath.

FIG. 19 shows a handle set 156 for controlling various functions of the closure device, discussed above. For example, the illustrated handle set 156 includes a plurality of control knobs 158 that allow an operator to move, for example, the first and second needles 122, 124 relative to the vessel 113 (see, e.g., FIGS. 6-8). A hub or sleeve 162 is inserted over the closure apparatus 119 adjacent to the handle set 156 so that suture material can be wound around sleeve 162 to form a portion of a pre-tied knot. Extra suture material is stored inside the handle set 156 on a spool (not shown) so that the suture material can be wrapped around the sleeve 162. The suture material supplied from the handle set 156 is integrally connected to the suture material 150 deployed across the opening in the vessel, as described in connection with FIGS. 1-18.

Figure 20:
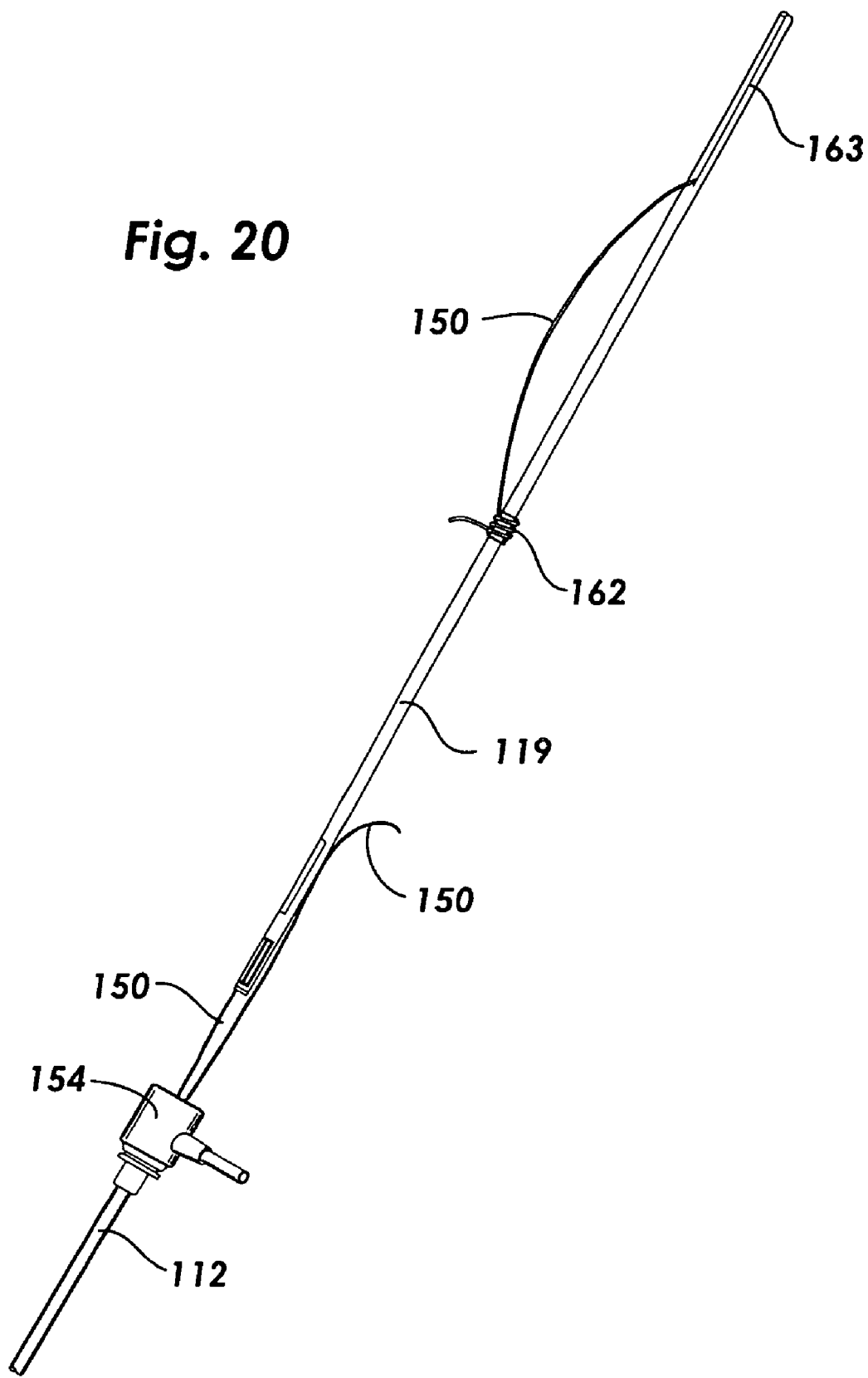
FIG. 20 is a perspective view, partly in section, of the vascular closure device of FIG. 2 showing the vascular closure device being retracted away from the hub and the sheath and showing the pre-tied knot formed around a sleeve coupled to the vascular closure device.
Figure 21:
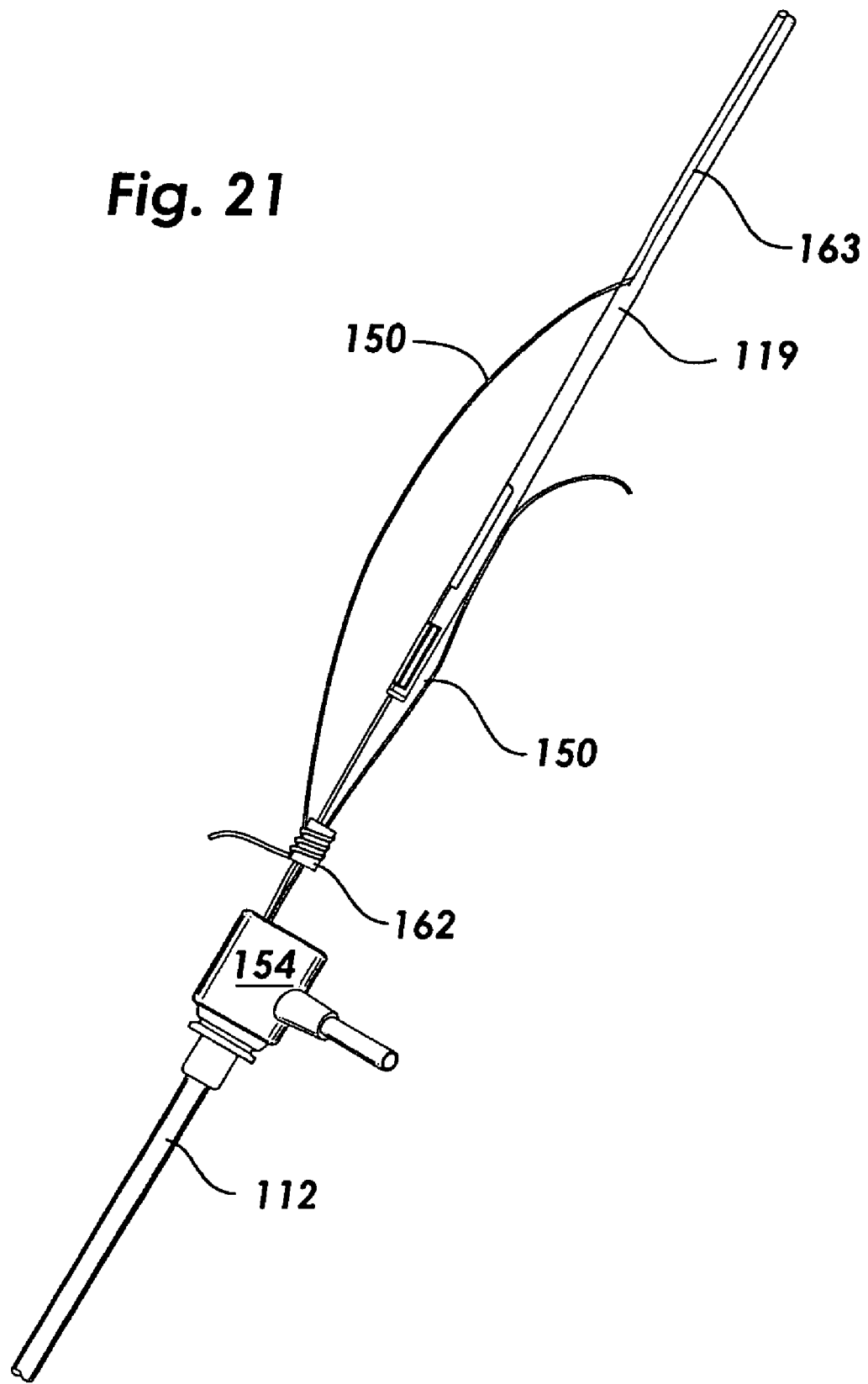
FIG. 21 is a perspective view of the closure device of FIG. 2 showing the pre-tied knot formed around the sleeve being removed from the closure device.
Figure 22:
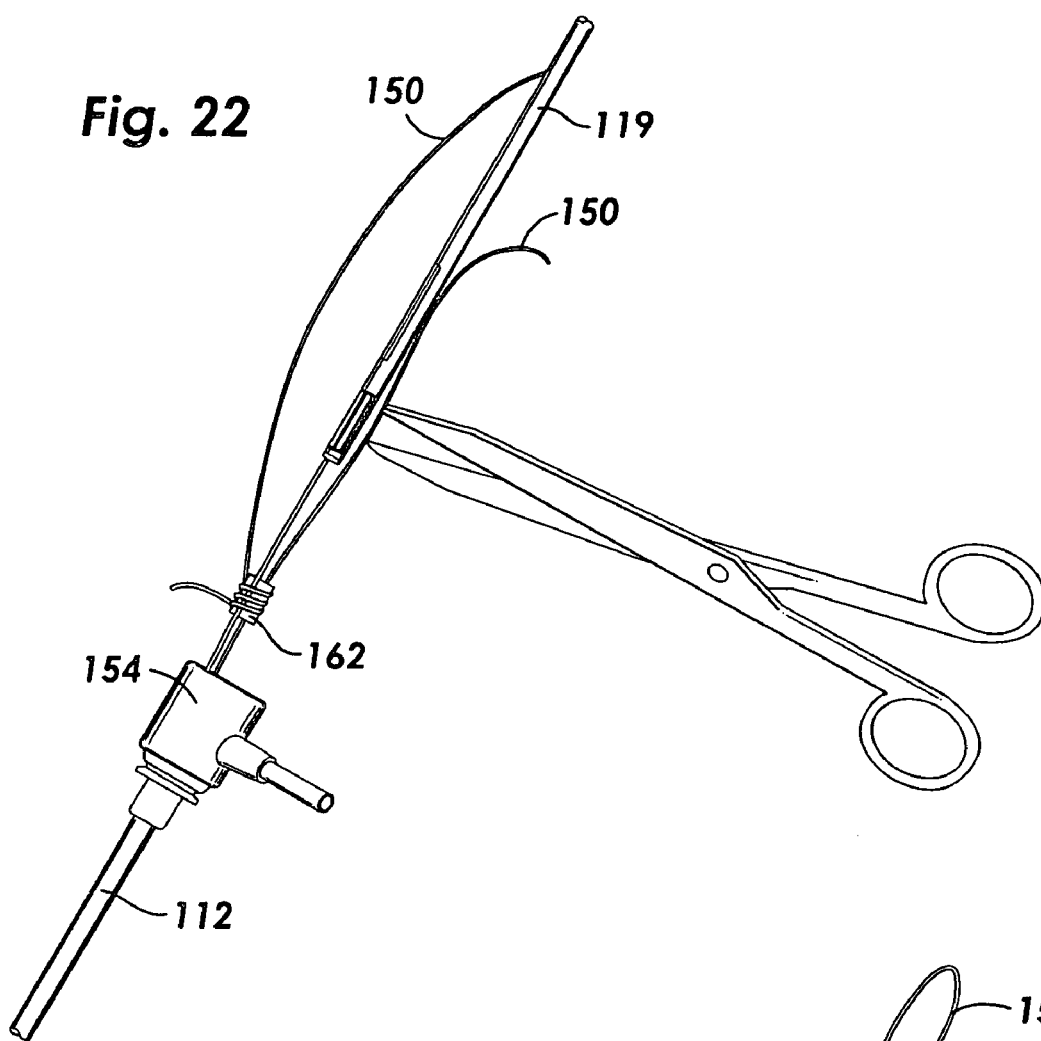
FIG. 22 is a perspective view of the hub portion of the sheath and the vascular closure device, and showing the distal end of the suture being cut after the vascular closure device has been retracted out of the sheath and the hub.
Figure 23:
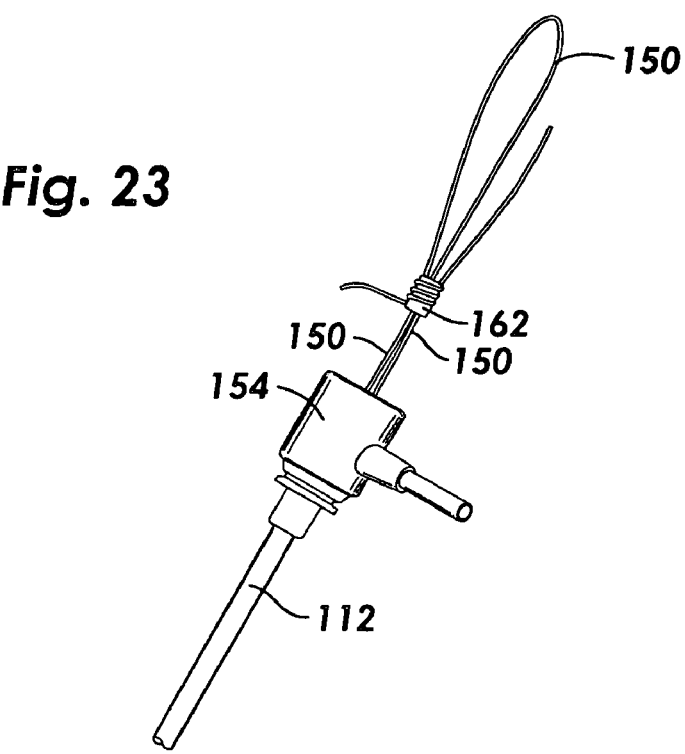
FIG. 23 is a perspective view of the handle set of FIG. 18 illustrating the distal or cut end of the suture being threaded through the sleeve holding the pre-tied knot.
Figure 24:
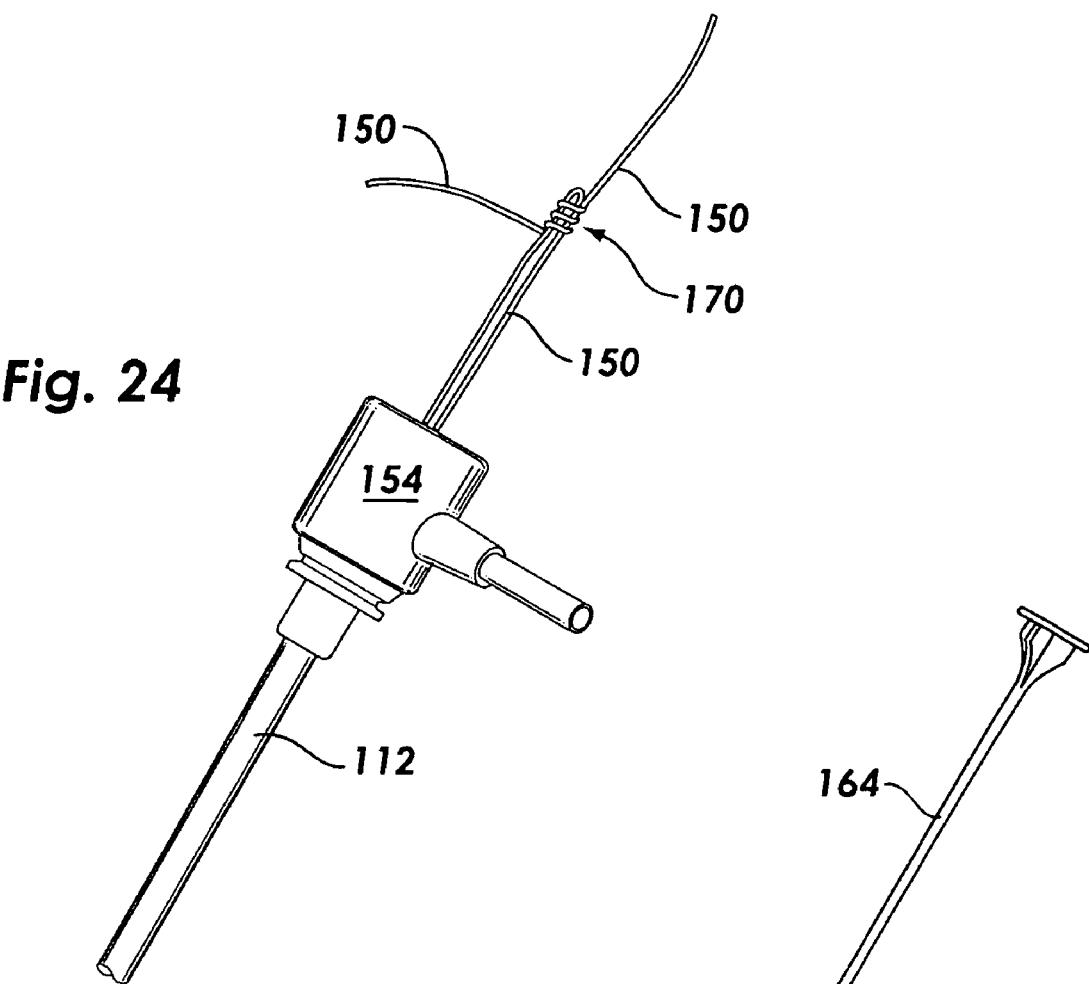
FIG. 24 is a perspective view of the closure device showing the sleeve being removed from the pre-tied knot so that the knot can be pushed down around the vessel opening.
Figure 25:
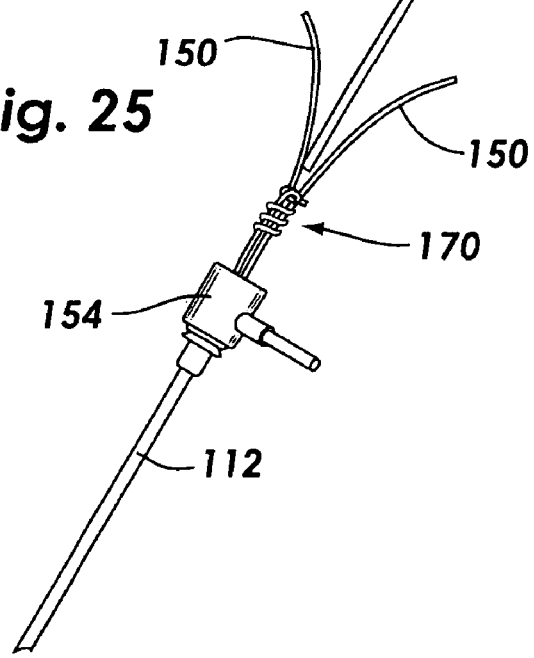
FIG. 25 is a perspective view showing a knot pusher engaging the pre-tied knot to push the knot down through the sheath to approximate tissue surrounding the vessel opening.

After the closure device 119 has been removed from the sheath 112, the free end of the suture 150 continues to be held against the body of the device 119 by the snare. As shown in FIG. 20, after the device 119 has been removed from the sheath 112 and hub 154, only the suture 150 remains extending down from the suture device 119 and through sheath 112. The sleeve 162 is thereafter detached from the handle set and slid down over the suture device 119. The suture 150 above sleeve 162 is "peeled" from within a slit 163 formed in the suture device body 119. After the sleeve 162 has been completely removed from the suture device body 119, as shown in FIG. 21, the suture material 150 that remains above sleeve 162 is pulled completely away from the suture device body 119 by pulling the suture from the slit 163 formed along the body 119. Since the free end of suture 150 remains tightly against one of the needles by the snare, described below, a new free end must be created. As shown in FIG. 22, a pair of scissors or other instrument is used to cut the suture 150 just below the location where the suture 150 is being held tightly against one of the needles by the snare (not shown in FIG. 22). Thereafter, the closure device 119 is completely separated from the hub 154 and vessel 112. The free end of suture 150, having already passed through the sleeve 162 (and consequently through the pre-tied portion of the suture material, which allows the pre-tied knot to automatically form) when the sleeve 162 is slid down over the closure apparatus 119, joins the pre-tied or coiled portion of suture 150 around the sleeve 162 to form the pre-tied knot. To finalize the knot, the sleeve 162 must be removed, which is accomplished by moving the sleeve 162 down and allowing the pre-tied knot to be cinched. Thereafter, the sleeve 162 can be pulled up over the cinched knot. To cinch the knot down around the opening in the vessel, a knot pusher 164 (FIG. 25) is brought into engagement with the knot so it can be pushed down through sheath 112.

Figure 26:
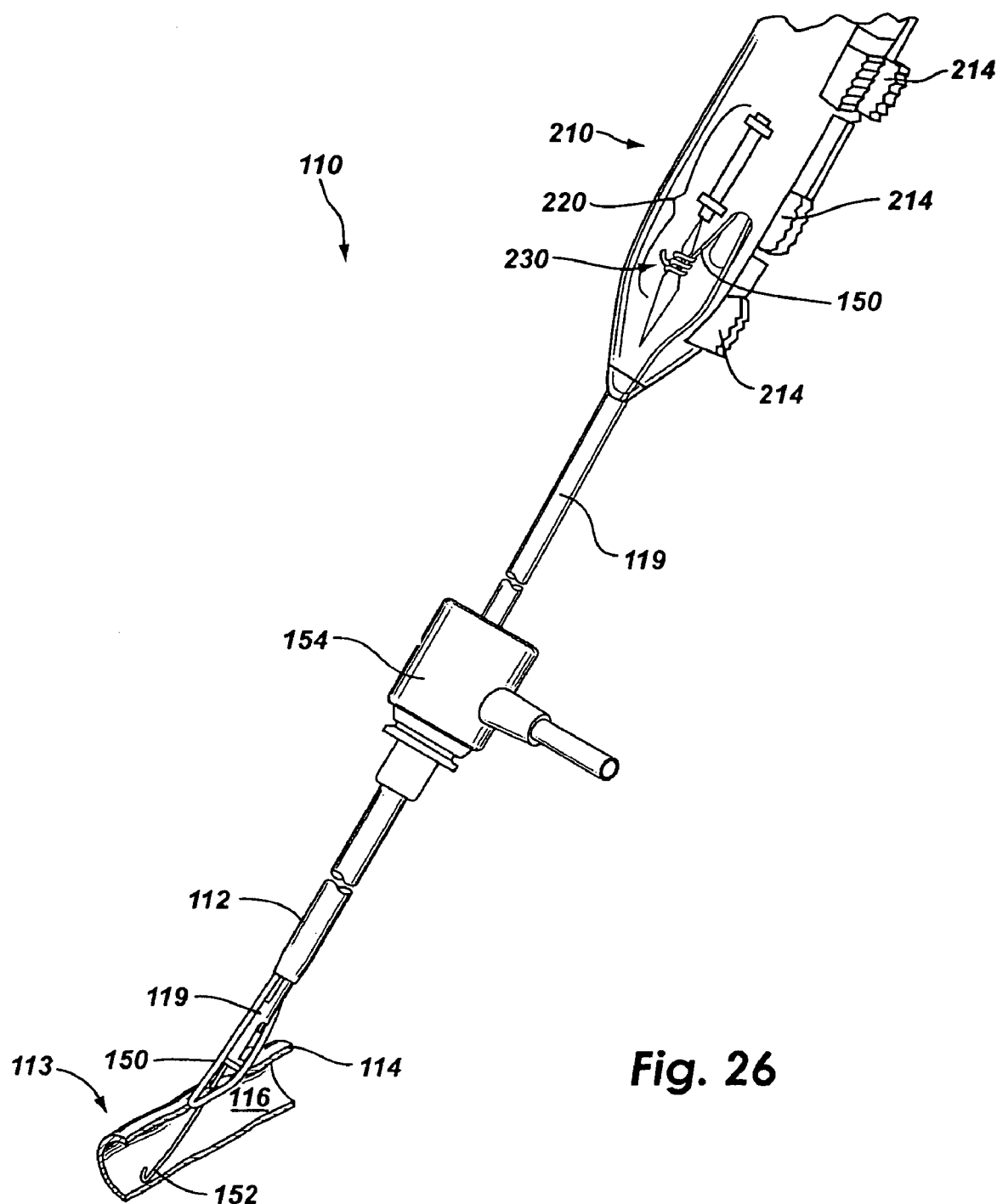
FIG. 26 is a perspective view of a vascular closure device further comprising a handle set having a pre-tied knot in combination with a needle threader to assist in deploying a pre-tied knot in connection with the present invention.
Figure 27:
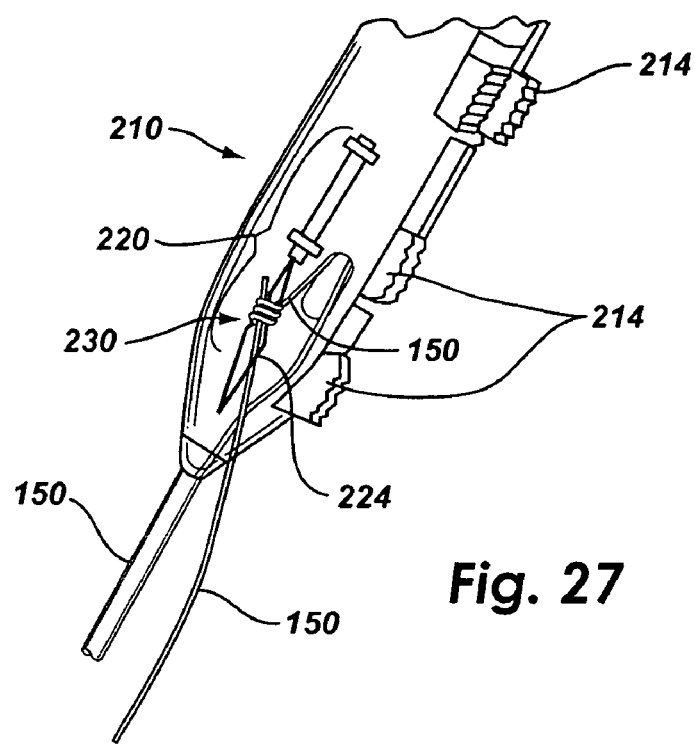
FIG. 27 is a perspective view of the handle set of FIG. 27 showing the free end of the suture being inserted through the needle threader coupled to the handle set.
Figure 28:
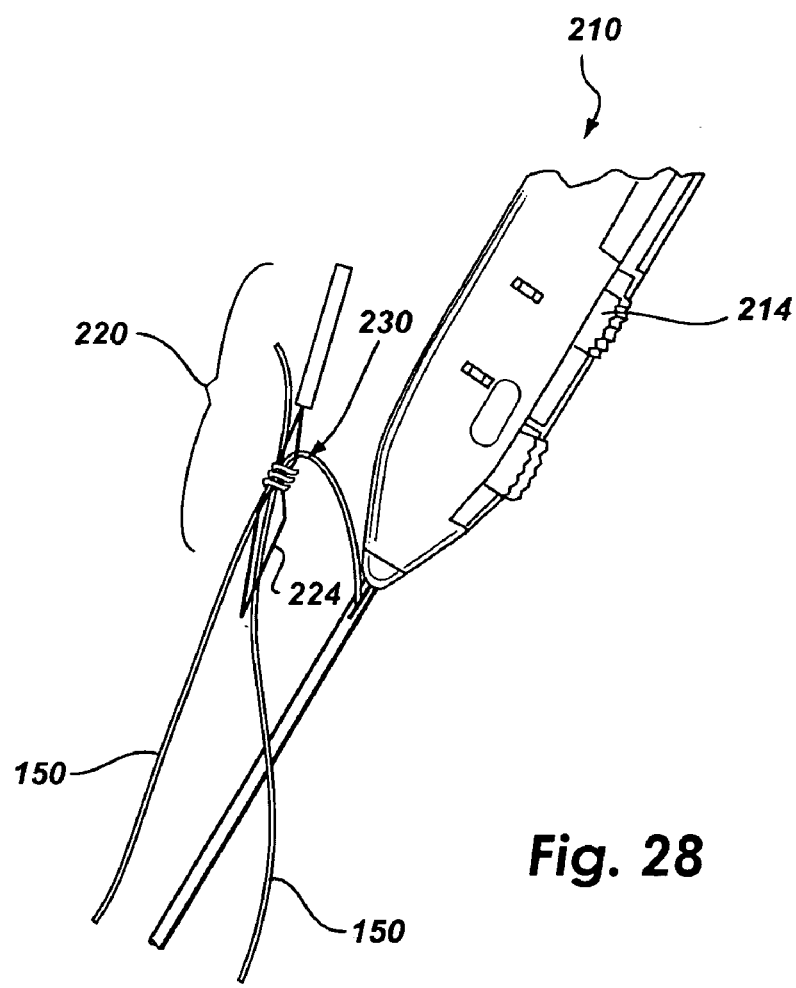
FIG. 28 is a perspective view of the handle set of FIG. 26 showing the needle threader being removed from the handle set so that a pre-tied knot can be pushed down adjacent the opening in the vessel wall to approximate tissue surrounding the vessel opening.
Figure 29:
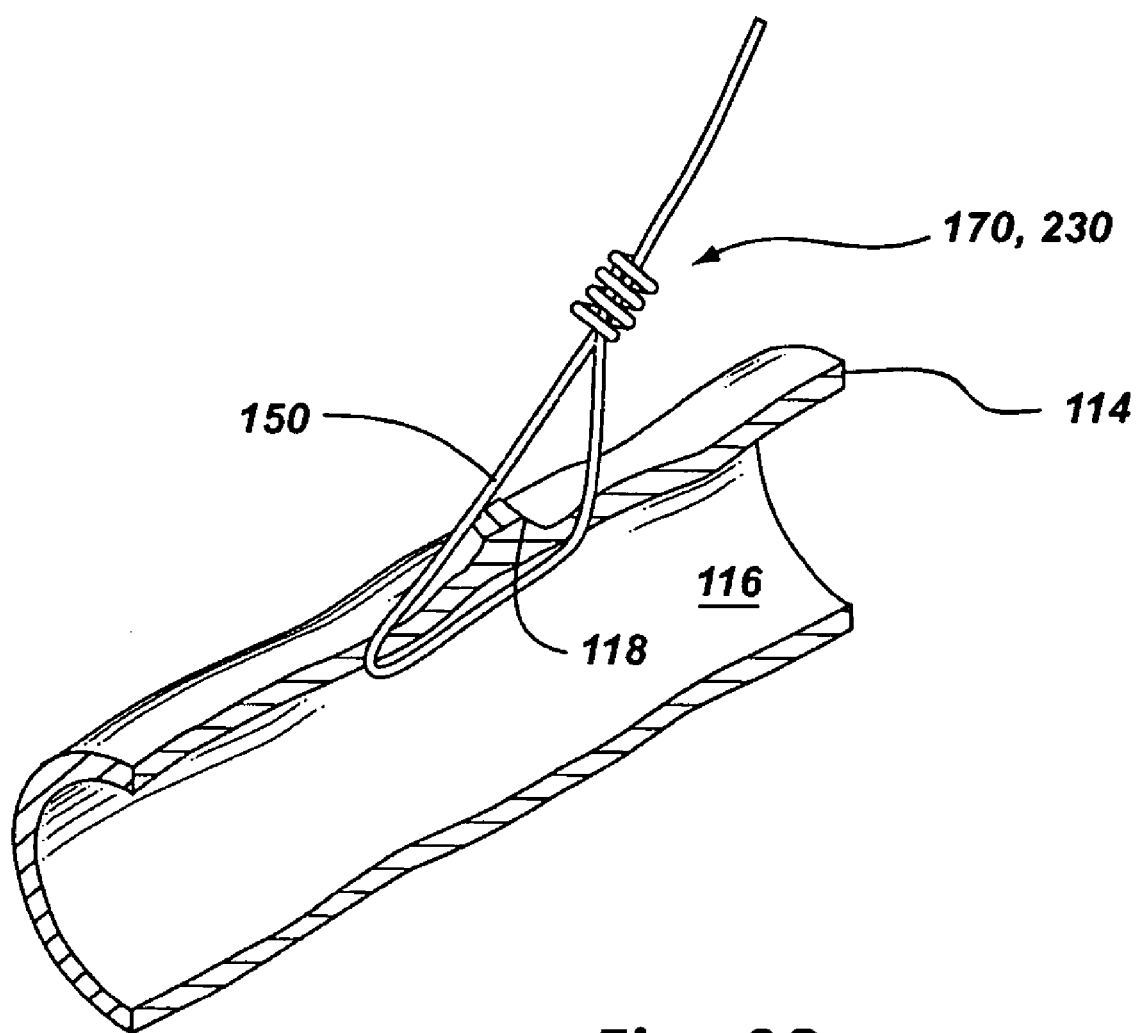
FIG. 29 is a perspective view of the knot being cinched around the vessel opening.

An alternative embodiment of a handle set is shown in FIGS. 26-28. In the alternative embodiment, a handle set 210 holds a needle threader 220. Handle set 210 includes a plurality of control knobs 214 that manipulate the various components of the suture device 110. A length of suture 150 is coiled around a needle threader 220 to automatically form a pre-tied portion of a pre-tied knot 230. Excess suture material 150 is held inside of handle set 210 on a spool (not shown). After the closure device 119 is removed from the sheath 112 (similar to the method described in connection with FIGS. 1-25), a free end of the suture 150 is directed or extended through the pre-tied portion to automatically form a pre-tied knot 230 on the needle threader 220, as shown in FIG. 27. Thereafter, the needle threader 220 including the pre-tied knot is removed from the handle set 210 (FIG. 28). A resulting knot 230 is then removed from the needle threader and a knot pusher (similar to the knot pusher 164 shown in FIG. 25) pushed down so that tissue can be approximated adjacent vessel opening 118, as shown in FIG. 29.

Those skilled in the art will understand that any suitable type of knot 170 may be utilized in connection with the present invention without departing from the scope and spirit thereof. That is, any suitable knot that can be cinched down toward the vessel opening 118 that can be used to effectively approximate tissue can be utilized according to the present invention.

While this invention has been described with reference to certain specific embodiments and examples, it will be recognized by those skilled in the art that many variations are possible without departing from the scope and spirit of this invention. The invention, as defined by the claims, is intended to cover all changes and modifications of the invention which do not depart from the spirit of the invention. The words "including" and "having," as used in the specification, including the claims, shall have the same meaning as the word "comprising."

The invention claimed is:

1. A vascular closure device, comprising:
a first needle and a second needle both of which are configured to move between a retracted position and an extended position relative to a sheath;
a suture configured to move with the first needle from the retracted position to the extended position;
a snare configured to move with the second needle from the retracted position to the extended position, the snare comprising a loop portion configured to grasp the suture after the first and second needles are in the extended position and the first needle and suture extend within the loop portion of the snare; and
a pre-tied knot disposed on a proximal end of the suture such that a distal end of the suture and the second needle can be directed through the pre-tied knot to approximate tissue surrounding a vascular opening.

2. A vascular closure device according to claim 1 wherein the snare comprises a wire loop having a memory that causes the wire loop to open in a repeatable orientation.

3. A vascular closure device according to claim 1 wherein the first needle and the second needle each extend outward and away from a body of the vascular closure device at an angle of 3° to 20°.

4. A vascular closure device according to claim 1, further comprising a handle set to allow an operator to control movement of the snare and the suture, and wherein the pre-tied knot on the proximal end of the suture is releasably attached to the handle set.

5. A vascular closure device according to claim 1 wherein when the first needle and the second needle are both in the extended position, the snare is configured to grasp the suture so that the suture can move with the snare and the second needle as the second needle moves back to the retracted position.

6. A vascular closure device according to claim 1 wherein the pre-tied knot is configured to form a slidable knot that is capable of cinching down when the distal end of the suture is threaded through the pre-tied knot.

7. A vascular closure device, comprising:
an anchor configured to extend through an opening in a blood vessel, the anchor being configured to move between a contracted configuration where the anchor is sized to fit through the opening in the blood vessel and an expanded configuration where the anchor is too large to fit through the opening in the blood vessel;
a snare configured to be inserted through a wall of the blood vessel at a location that is laterally adjacent to the opening in the blood vessel, the snare comprising a loop portion;
a suture and a needle combination configured to be inserted through the wall of the blood vessel at another location that is laterally adjacent to the opening, the loop portion of the snare also being configured to receive the suture and needle combination after the snare and the suture and needle combination are inserted through the wall of the blood vessel and to grasp the suture in the blood vessel and retract the suture through the wall of the blood vessel;
wherein the vascular closure device is configured to close the opening in the blood vessel.

8. A vascular closure device according to claim 7 wherein the snare comprises a wire loop having a memory that causes the wire loop to open in a repeatable orientation.

9. A vascular closure device according to claim 7 wherein the snare and the suture and needle combination each move between a retracted position and an extended position to allow the snare and the suture to be inserted through the wall of the blood vessel.

10. A vascular closure suturing device according to claim 7 further comprising a handle set to allow an operator to control movement of the snare and the suture.

11. A vascular closure device according to claim 7, further comprising a pre-tied knot positioned to receive the suture after the suture is retracted through the wall of the blood vessel by the snare.

12. A vascular closure device according to claim 7 comprising a first needle and a second needle, the first needle being configured to insert the suture through the wall of the blood vessel and the second needle being configured to insert the snare through the wall of the blood vessel.

13. A method of closing a vascular opening utilizing a vascular closure device comprising:
inserting a sheath into a vessel through a vessel opening;
inserting a snare into the vessel on a first side of and laterally adjacent the vessel opening, the snare comprising a loop portion;
inserting a needle with a suture into the vessel on a second side of and laterally adjacent the vessel opening;
positioning the needle with the suture inside the loop portion of the snare after inserting the snare and the needle with suture into the vessel;
grasping the suture with the loop portion of the snare;
pulling the suture across the vessel opening and through the vessel on the first side of the vessel opening;
directing the distal end of the suture through a pre-tied knot formed at a proximal end of the suture to create a knot to approximate tissue surrounding the vessel opening.

14. The method of claim 13, further comprising cinching the knot to approximate tissue surrounding the vessel opening.

15. The method of claim 13, further comprising anchoring the sheath inside the vessel with a pair of extendable feet.

16. The method of claim 13, further comprising extending a safety wire into the vessel opening such that the safety wire can be used to facilitate reinserting the sheath if the snare fails to grasp the suture.

17. The method of claim 13, further comprising disengaging the sheath from the vessel and withdrawing the sheath from the vessel opening such that the suture remains extended across the vessel opening.

18. The method of claim 13, further comprising tightening the suture such that the suture approximates tissue surrounding the vessel opening.

19. A vascular closure device, comprising:
a needle positioned at a distal end of the vascular closure device, the needle being configured to move between a retracted position and an extended position;
a suture having a free end configured to move with the needle from the retracted position to the extended position, wherein a portion of the suture extends lengthwise from a tip of the needle toward a proximal end of the vascular closure device, the portion of the suture being positioned outside of the needle; and
a pre-tied knot positioned at a proximal end of the vascular closure device;
a snare comprising a loop portion;
wherein the vascular closure device is configured to pass the loop portion of the snare through a wall of the blood vessel at a first location on the wall laterally adjacent to a tissue puncture, pass the suture and the needle through the wall of the blood vessel at a second location on the wall laterally adjacent to the tissue puncture, and then pass the suture and needle into the loop portion, the loop portion of the snare being configured to grasp the suture at a location spaced from the free end and retract the suture through the wall of the blood vessel and on through the pre-tied knot to approximate tissue surrounding an opening in the blood vessel.

20. The vascular closure device according to claim 19 wherein the pre-tied knot is provided on a sleeve that is configured to move from the proximal end of the vascular closure device to the distal end of the vascular closure device.

21. A method of closing an opening in a blood vessel with a vascular closure device, comprising:
inserting a needle and a suture together through a wall of the blood vessel at a location that is adjacent to the opening;
inserting a snare through the wall of the blood vessel at another location that is adjacent to the opening, the snare comprising a loop portion;
positioning the needle and the suture within the loop portion of the snare after the needle and suture and the snare are inserted through the wall of the blood vessel;
grasping the suture with the loop portion of the snare after removing the needle from within the loop portion;
withdrawing the suture through the wall of the blood vessel; and
tightening the suture to close the opening in the blood vessel.

22. The method of claim 21 wherein tightening the suture includes passing the suture through a pre-tied knot and tightening the knot.

23. The method of claim 21 wherein inserting the suture through the wall includes inserting a needle coupled to the suture through the wall.

24. The method of claim 21 wherein inserting the snare through the wall includes inserting a needle that includes the snare through the wall.

25. The method of claim 21 comprising extending a safety wire through the opening.

26. The method of claim 21 comprising securing the vascular closure device in the blood vessel.

27. A vascular closure device, comprising:
a first needle and a second needle both of which are configured to move between a retracted position and an extended position relative to a sheath;
a suture and a suture pusher configured to move with the first needle from the retracted position to the extended position;
a snare configured to move with the second needle from the retracted position to the extended position, the snare including a wire loop having a memory that causes the wire loop to open in a repeatable orientation; and
a pre-tied knot disposed on a proximal end of the suture such that a distal end of the suture can be directed through the pre-tied knot to approximate tissue surrounding a vascular opening;
the, suture pusher, suture and first needle being positionable inside the wire loop of the snare after the first and second needles move to the extended position;
wherein the wire loop grasps the suture after the first needle and the suture pusher are removed from inside the wire loop.

28. A method of closing a vascular opening utilizing a vascular closure device comprising:
inserting a sheath into a vessel through a vessel opening;
inserting a snare into the vessel at a first location laterally adjacent to the vessel opening, the snare including a wire loop;
inserting a suture with a needle into the vessel at a second location laterally adjacent to the vessel opening;
inserting the suture with the needle into the wire loop;
extending the wire loop across the vessel opening to grasp the suture;
pulling the suture across the vessel opening and through the vessel on the first side of the vessel opening;
directing the distal end of the suture through a pre-tied knot formed at a proximal end of the suture to create a knot to approximate tissue surrounding the vessel opening.

* * * * *